US007122491B2

(12) United States Patent
Barton et al.

(10) Patent No.: US 7,122,491 B2
(45) Date of Patent: Oct. 17, 2006

(54) METHOD OF INCREASING THE LIFETIME OF A HYDRO-OXIDATION CATALYST

(75) Inventors: David G. Barton, Midland, MI (US); Robert G. Bowman, Midland, MI (US); George E. Hartwell, Midland, MI (US); Howard W. Clark, Lake Jackson, TX (US); Alexander Kuperman, Orinda, CA (US)

(73) Assignee: Dow Global Technologies Inc., Midland, MI (US)

( * ) Notice: Subject to any disclaimer, the term of this patent is extended or adjusted under 35 U.S.C. 154(b) by 392 days.

(21) Appl. No.: 10/484,328

(22) PCT Filed: Jul. 31, 2002

(86) PCT No.: PCT/US02/24339

§ 371 (c)(1),
(2), (4) Date: Jan. 21, 2004

(87) PCT Pub. No.: WO03/011454

PCT Pub. Date: Feb. 13, 2003

(65) Prior Publication Data

US 2004/0171893 A1 Sep. 2, 2004

Related U.S. Application Data

(60) Provisional application No. 60/309,345, filed on Aug. 1, 2001.

(51) Int. Cl.
*B01J 38/00* (2006.01)
*C07D 301/10* (2006.01)

(52) U.S. Cl. ............... 502/20; 502/120; 502/326; 502/344; 549/533; 549/534; 549/536; 549/537

(58) Field of Classification Search ............... 502/20, 502/120, 326, 344; 549/533, 534, 536, 537
See application file for complete search history.

(56) References Cited

U.S. PATENT DOCUMENTS

| | | | | |
|---|---|---|---|---|
| 3,923,843 | A | 12/1975 | Wulff | 260/348.5 L |
| 5,623,090 | A | 4/1997 | Haruta et al. | 568/360 |
| 5,859,265 | A | 1/1999 | Müller et al. | 549/531 |
| 5,932,750 | A | 8/1999 | Hayashi et al. | 549/523 |
| 5,939,569 | A | 8/1999 | Jones et al. | 549/512 |
| 5,965,754 | A | 10/1999 | Clark et al. | 549/533 |
| 6,008,389 | A | 12/1999 | Grosch et al. | 549/533 |
| 6,031,116 | A | 2/2000 | Bowman et al. | 549/523 |
| 6,034,028 | A | 3/2000 | Hayashi et al. | 502/243 |
| 6,252,095 | B1 | 6/2001 | Hayashi et al. | 549/523 |
| 6,255,499 | B1 | 7/2001 | Kuperman et al. | 549/523 |
| 6,284,696 | B1 | 9/2001 | Koya et al. | 502/64 |
| 6,323,351 | B1 | 11/2001 | Bowman et al. | 549/536 |
| 6,362,349 | B1 | 3/2002 | Kuperman et al. | 549/533 |
| 6,524,991 | B1 | 2/2003 | Bowman et al. | 502/242 |
| 6,562,986 | B1 | 5/2003 | Bowman et al. | 549/523 |
| 6,603,028 | B1 | 8/2003 | Weisbeck et al. | 549/536 |
| 6,646,142 | B1 | 11/2003 | Meima et al. | 549/536 |
| 6,670,491 | B1 | 12/2003 | Bowman et al. | 549/523 |
| 2002/0137625 | A1* | 9/2002 | Jost et al. | 502/158 |

FOREIGN PATENT DOCUMENTS

| | | |
|---|---|---|
| CA | 2 370 796 | 11/2000 |
| CA | 2 370 815 | 11/2000 |
| CA | 2 371 030 | 12/2000 |
| DE | 19804712 | 8/1999 |
| EP | 0709360 A1 | 5/1996 |
| EP | 0734764 A2 | 10/1996 |
| EP | 1005907 A1 | 6/2000 |
| EP | 1040869 A2 | 10/2000 |
| EP | 1048660 A1 | 11/2000 |
| WO | WO 97/25143 | 7/1997 |
| WO | WO 98/00413 | 1/1998 |
| WO | WO 98/00414 | 1/1998 |
| WO | WO 98/00415 | 1/1998 |
| WO | WO 99/00188 | 1/1999 |
| WO | WO 00/35893 | 6/2000 |
| WO | WO 00/59632 | 10/2000 |
| WO | WO 00/59633 | 10/2000 |
| WO | WO 01/41926 | 6/2001 |

OTHER PUBLICATIONS

"Activation and Regeneration of a Hydro-Oxidation Catalyst", filed Sep. 25, 2003, U.S. Appl. No. 10/148,804, Applicants: Deborah H. Parker et al. (Corresponds to WO 01/41926).

(Continued)

*Primary Examiner*—Porfirio Nazario-Gonzalez
(74) *Attorney, Agent, or Firm*—Marie F. Zuckerman

(57) ABSTRACT

A method of increasing the lifetime of a hydro-oxidation catalyst comprising, preferably, gold, silver, or mixtures thereof, and optionally one or more promoters, on a titanium-containing support, such as a titanosilicate or titanium dispersed on silica. The method of the invention involves contacting the catalyst support with a hydroxy-functionalized organosilicon compound, a carboxy-functionalized organosilicon compound, or a mixture of hydroxy- and carboxy-functionalized organosilicon compounds, such as, sodium methyl siliconate or (2-carboxypropyl)tetramethyldisiloxane. The contacting is preferably conducted during deposition of the catalytic metal(s) and optional promoters (s) onto the support. A catalyst composition and hydro-oxidation process utilizing the silicon-treated catalyst support are also claimed.

30 Claims, No Drawings

OTHER PUBLICATIONS

Derwent Abstract 1999-445378, "Extending the Useful Life of Gold-Coated Supported Catalysts for the Gas-Phase Epoxidation of Unsaturated Hydrocarbon, Especially Propene", Corresponds to DE 19804712 (1999).

Derwent Abstract 1997-364851. "Oxidation Catalyst Used for Preparing Epoxide(s) From Olefin(s)—Composed of Titanium or Vanadium Silicalite with Zeolite Structure Containing Lanthanide Metal(s)", Corresponds to WO 9725143 (1997).

"Method of Preparing a Catalyst Containing Gold and Titanium," filed April 7, 2000, U.S. Appl. No. 09/544,742 Applicants: Alex Kuperman et al. (Corresponds to WO 00/59633).

"Method of Preparing a Catalyst Containing Gold and Titanium," filed Mar. 15, 2004, U.S. Appl. No. 10/800,963 Applicants: Robert G. Bowman et al. (Corresponds to WO 00/59633, and a continuation of U.S. Appl. No. 09/544,742).

* cited by examiner

METHOD OF INCREASING THE LIFETIME OF A HYDRO-OXIDATION CATALYST

CROSS-REFERENCE TO RELATED APPLICATIONS

This application is a 371 continuation of International Patent Application PCT/US02/24339, filed Jul. 31, 2002, which claims the benefit of U.S. Provisional Application Ser. No. 60/309,345, filed Aug. 1, 2001.

This invention pertains to a method of increasing the lifetime of a hydro-oxidation catalyst.

Hydro-oxidation catalysts find utility in hydro-oxidation processes, which involve the oxidation of organic compounds, such as hydrocarbons, by oxygen in the presence of hydrogen to form partially-oxidized organic compounds, such as partially-oxidized hydrocarbons. One important hydro-oxidation process involves the partial oxidation of an olefin, such as propylene, with oxygen in the presence of hydrogen to form an olefin oxide, such as propylene oxide. Olefin oxides, such as propylene oxide, are used inter alia to alkoxylate alcohols to form polyether polyols, such as polypropylene polyether polyols, which find significant utility in the manufacture of polyurethanes and synthetic elastomers. Another important hydro-oxidation process involves the partial oxidation of an alkane, such as propane or isobutane, with oxygen in the presence of hydrogen to form useful partially-oxidized hydrocarbons, such as acetone or t-butanol, respectively.

The hydro-oxidation of olefins to olefin oxides has been described in several international patent publications, for example, WO 97/34692, WO 98/00413, WO 98/00414, WO 98/00415, and WO 00/59632. This prior art discloses hydro-oxidation catalysts comprising gold on a titanium-containing support, such as titania, a titanosilicate, or titanium dispersed on a carrier. U.S. Pat. No. 5,939,569 extends the concept of olefin hydro-oxidation to catalysts comprising gold on zirconia supports. Along similar lines, international patent publications WO 99/00188, WO 00/35893, and WO 00/07964 disclose catalysts comprising silver on a titanium-containing support for the hydro-oxidation of olefins to olefin oxides. Other references, such as WO 96/02323 and WO 97/47386 disclose a catalyst comprising a platinum group metal or a noble metal deposited on titanium or vanadium silicalite for the hydro-oxidation of olefins to olefin oxides. Likewise, references, such as WO 97/25143, disclose catalysts comprising a lanthanide rare earth on titanium or vanadium silicalite for the hydro-oxidation of olefins to olefin oxides. As taught in international patent publications WO 98/00414 and WO 00/59632, the hydro-oxidation catalyst can optionally comprise one or more promoter metals selected, for example, from Group 1, Group 2, the lanthanide rare earths, and the actinide metals of the Periodic Table.

Additional art, such as EP-A1-0,709,360 and U.S. Pat. No. 5,623,090 disclose a catalyst comprising gold deposited on titania or titania dispersed on silica for the hydro-oxidation of an alkane, such as isobutane or propane, to form a partially oxygenated hydrocarbon, such as t-butanol or acetone, respectively.

Although hydro-oxidation catalysts show an acceptable activity in the initial stages of the hydro-oxidation process, generally these catalysts exhibit a decrease in activity with the passing of time. At some point in time, the catalyst activity decreases to an unacceptable level, and a remedy must be sought to increase catalyst activity to an acceptable level. One such remedy involves increasing the hydro-oxidation process temperature, which generally increases catalytic activity and increases conversion of the hydrocarbon reactant. A rise in process temperature, however, may lead to a disadvantageous decrease in selectivity to the desired partially-oxygenated product, such as an alcohol, ketone, aldehyde, or olefin oxide. Moreover, increasing the process temperature may lead to an increased deactivation rate by an increased metal sintering rate or by detrimental changes at the active sites of the catalyst or in the catalyst support. When increasing process temperature is an insufficient remedy, the hydro-oxidation process may be forced to shut down for a separate catalyst regeneration or replacement procedure. Process interruption is generally undesirable from the perspective of higher costs and lower productivity. One standard catalyst regeneration method involves heating the deactivated catalyst for several hours at elevated temperature in the presence of a regeneration gas, such as, an oxygen-containing gas. The regeneration temperature is typically higher than the hydro-oxidation process temperature; consequently, the time and energy needed to cycle the catalyst between the hydro-oxidation stage and the regeneration stage, and back again, makes frequent regeneration undesirable. As a further disadvantage, process equipment must be designed to withstand the higher regeneration temperature. With each regeneration cycle, a percentage of the catalyst activity may be irretrievably lost, until at some point the catalyst lifetime is exhausted, and the catalyst must be replaced.

In view of the above, it would be desirable to improve on the methods of increasing the lifetime of a hydro-oxidation catalyst. Recently, certain prior art, represented by International Patent Publications WO 99/43431 and WO 00/64582, disclose modification treatments of the catalyst support with silylation agents for the purpose of increasing catalyst lifetime. The silylation of the support is taught to be conducted at any time before or after fixing gold or silver particles onto the support. Disadvantageously, the silylation is provided as an additional process step in the catalyst synthesis. A variety of silylation agents are disclosed including organic silanes, organic silyl amines, organic silazanes, and organic silyl amides; but disadvantageously, many of the disclosed silylation agents are expensive or difficult to handle. As a further disadvantage, the catalysts prepared exhibit low activity, which offsets the advantage of longer catalyst lifetime. In addition, the aforementioned references are silent with respect to hydroxy-functionalized and/or carboxy-functionalized silylation agents.

In view of the above, it would be desirable to discover a method of increasing the lifetime of a hydro-oxidation catalyst while maintaining acceptable levels of catalytic activity and selectivity. It would be more desirable, if the method of increasing catalyst lifetime not only maintained acceptable levels of catalyst activity and selectivity, but also provided for a high hydrogen efficiency, as measured by a low molar ratio of water to oxidized product produced. Towards this end, a molar ratio of water to oxidized product of less than 4/1 is a desirable target. It would be even more desirable, if the method of increasing catalyst lifetime was easy to implement and inexpensive. Finally, it would be most desirable, if the method to increase catalyst lifetime could be integrated into the synthesis of the hydro-oxidation catalyst itself, such that no extra equipment or extra process steps, such as pretreatment of the catalyst support or post-treatment of the synthesized catalyst, were needed to effect the lifetime enhancement. Towards this end, it would be desirable, if the method to increase catalyst lifetime was compatible with catalytic metal depositions from aqueous solution.

This invention provides for a novel process of enhancing the lifetime of a hydro-oxidation catalyst. For the purposes of this invention, a hydro-oxidation catalyst shall comprise at least one catalytic metal deposited onto a catalyst support, the catalyst being capable of catalyzing a hydro-oxidation process, preferably, the conversion of a hydrocarbon with oxygen in the presence of hydrogen to form a partially-oxidized hydrocarbon. The novel process of this invention, which extends catalyst lifetime, comprises contacting the catalyst support of the hydro-oxidation catalyst with a hydroxy-functionalized organosilicon compound, a carboxy-functionalized organosilicon compound, or a mixture of hydroxy- and carboxy-functionalized organosilicon compounds. In the process of this invention, the contacting of the catalyst support with the hydroxy-functionalized and/or carboxy-functionalized organosilicon compound is conducted under contacting conditions sufficient to increase the lifetime of the hydro-oxidation catalyst.

The unique process of this invention advantageously extends the lifetime of a hydro-oxidation catalyst, preferably, a hydro-oxidation catalyst comprising gold, silver, or mixtures thereof, on a titanium-containing support. More advantageously, the unique process of this invention extends catalyst lifetime while maintaining acceptable catalyst activity and selectivity and while maintaining good hydrogen efficiency of the hydro-oxidation process. Even more advantageously, the unique process of this invention, which extends catalyst lifetime, is easy to implement and cost effective, in that the process involves one simple contacting step with at least one readily-available and low-cost additive, namely, an hydroxy-functionalized and/or carboxy-functionalized organosilicon compound. In a more preferred embodiment of this invention, the contacting of the hydroxy-functionalized and/or carboxy-functionalized organosilicon compound with the catalyst support is effected during the synthesis of the hydro-oxidation catalyst itself, most preferably, during the deposition of the catalytic metal component(s) onto the catalyst support. In this aspect, the process of the invention is compatible with catalytic metal depositions from aqueous solution. When carried out in this more preferred manner, the advantage of increased catalyst lifetime is obtained without special equipment and without additional process steps, such as a separate pretreatment of the catalyst support or a separate post-treatment of the synthesized catalyst. In another most preferred embodiment of this invention, the organosilicon reagent further comprises one or more promoter(s). In this most preferred embodiment, the organosilicon reagent can function beneficially in one or more capacities, specifically, to increase catalyst lifetime, to aid in the deposition of the catalytic metal(s) onto the support, and to deliver a promoter that is capable of increasing catalyst productivity, as defined hereinafter. All of the aforementioned advantages render the process of this invention uniquely attractive for increasing the lifetime of a hydro-oxidation catalyst.

In a second aspect, this invention provides for a hydro-oxidation catalyst composition comprising a catalytic metal selected from gold, silver, the platinum group metals, the lanthanide rare earths, and combinations thereof, on a support, the support being contacted with a hydroxy-functionalized organosilicon compound, a carboxy-functionalized organosilicon compound, or a mixture of hydroxy-functionalized and carboxy-functionalized organosilicon compounds.

The aforementioned catalyst composition is beneficially employed in a hydro-oxidation process, preferably, a hydro-oxidation process wherein a hydrocarbon, more preferably, an alkane or an olefin, is contacted with oxygen in the presence of hydrogen to form a partially-oxidized hydrocarbon, preferably, an alcohol, aldehyde, ketone, olefin oxide, or carboxylic acid. The composition of this invention, which incorporates a hydroxy-functionalized and/or carboxy-functionalized organosilicon compound onto the catalyst support, advantageously exhibits increased catalyst lifetime, as compared with similar catalysts that do not contain the aforementioned organosilicon compound.

In yet another aspect, this invention comprises a novel hydro-oxidation process comprising contacting a hydrocarbon with oxygen in the presence of hydrogen and in the presence of a unique hydro-oxidation catalyst under conditions sufficient to prepare a partially-oxidized hydrocarbon. The unique catalyst used in this process comprises a catalytic metal selected from gold, silver, the platinum group metals, the lanthanide rare earths, and combinations thereof, on a support, the support having been contacted with a hydroxy-functionalized organosilicon compound, a carboxy-functionalized organosilicon compound, or a mixture of hydroxy-functionalized and carboxy-functionalized organosilicon compounds.

The novel hydro-oxidation process of this invention produces useful partially-oxidized hydrocarbons, such as aldehydes, ketones, alcohols, olefin oxides, and carboxylic acids. Beneficially, the unique hydro-oxidation catalyst employed in this hydro-oxidation process exhibits acceptable activity, selectivity, and hydrogen efficiency, and improved lifetime, as compared with prior art catalysts.

In one of the novel processes of this invention, a method is provided of increasing the lifetime of a hydro-oxidation catalyst comprising a catalyst support and one or more catalytic metal components deposited thereon. The term "hydro-oxidation catalyst" shall mean that the catalyst can catalyze a hydro-oxidation process, preferably, a process wherein a hydrocarbon is contacted with oxygen in the presence of hydrogen to form a partially-oxidized hydrocarbon, such as an alcohol, an aldehyde, an olefin oxide, a ketone, and/or a carboxylic acid.

The aforementioned novel process of this invention, which improves catalyst lifetime, comprises contacting the catalyst support of the hydro-oxidation catalyst with a hydroxy-functionalized organosilicon compound, a carboxy-functionalized organosilicon compound, or a mixture of hydroxy-functionalized and carboxy-functionalized organosilicon compounds under contacting conditions sufficient to increase catalyst lifetime. The novel process of this invention advantageously extends catalyst lifetime, as compared with the lifetime of a catalyst having no contact of its support with said organosilicon compound. Moreover, the process extends catalyst lifetime while still maintaining good catalyst activity and selectivity and while maintaining good hydrogen efficiency in the hydro-oxidation process.

For clarity of explanation, several definitions are presented hereinafter. For the purposes of this invention, "catalyst lifetime" shall be defined as the time elapsed from the start of the hydro-oxidation process to the time at which the catalyst, after regeneration, has lost sufficient activity so as to render the catalyst useless, preferably, commercially useless. As used herein, "catalyst activity" shall be defined in terms of conversion, that being the mole or weight percentage of reactant, preferably hydrocarbon reactant, such as alkane or olefin, in the hydro-oxidation feedstream that is converted to products. As used herein, "selectivity"

shall be defined as the mole or weight percentage of converted reactant, preferably hydrocarbon reactant, that forms a specific oxidized product, such as, alcohol, aldehyde, ketone, olefin oxide, or carboxylic acid. In addition, water is formed as a by-product of this process, either during the partial oxidation of the hydrocarbon with oxygen or by the combustion of hydrogen with oxygen. Accordingly, the "hydrogen efficiency" of the hydro-oxidation process shall be measured by the ratio of moles of water formed to moles of oxidized product formed.

In another aspect, this invention provides for a novel hydro-oxidation catalyst composition comprising a catalytic metal selected from gold, silver, the platinum group metals, the lanthanide rare earths, and combinations thereof, on a support. In this aspect, the support is contacted with a hydroxy-functionalized organosilicon compound, a carboxy-functionalized organosilicon compound, or a mixture of hydroxy-functionalized and carboxy-functionalized organosilicon compounds. In a preferred embodiment of the catalyst composition, the catalyst support comprises a titanium-containing or vanadium-containing support. In a more preferred embodiment of the catalyst composition, the catalyst comprises gold, silver, or a combination of gold and silver, deposited onto a titanium-containing support.

In another preferred embodiment of this invention, the hydroxy-functionalized and/or carboxy-functionalized organosilicon compound is contacted with the catalyst support simultaneously with the deposition of the catalytic metal(s), for example, gold, silver, or mixture thereof, onto the catalyst support. In another more preferred embodiment, the contacting of the hydroxy-functionalized and/or carboxy-functionalized organosilicon compound with the catalyst support comprises an impregnation method, that method being well known to those skilled in the art.

In yet another aspect, this invention provides for a novel hydro-oxidation process comprising contacting a hydrocarbon with oxygen in the presence of hydrogen and in the presence of the aforementioned novel hydro-oxidation catalyst under conditions sufficient to prepare a partially-oxidized hydrocarbon. The novel catalyst, as noted hereinabove, comprises a catalytic metal selected from gold, silver, the platinum group metals, the lanthanide rare earths, and combinations thereof, on a support, wherein the support is contacted with a hydroxy-functionalized organosilicon compound, a carboxy-functionalized organosilicon compound, or a mixture of hydroxy-functionalized and carboxy-functionalized organosilicon compounds. This novel process beneficially can be used to prepare useful partially-oxidized hydrocarbons, preferably, aldehydes, alcohols, ketones, olefin oxides, and/or caxboxylic acids.

In general terms, the hydro-oxidation catalyst, which benefits from the unique synthetic process of this invention, comprises a catalyst support onto which one or more catalytic metals are dispersed. Any catalyst support and any catalytic metal(s) are suitably present, provided that the catalyst synthesized therefrom exhibits activity in a hydro-oxidation process, particularly, a process wherein a hydrocarbon is converted with oxygen in the presence of hydrogen into a partially-oxidized hydrocarbon. Non-limiting examples of suitable hydro-oxidation catalysts are described in the following references: WO 96/02323, WO 97/25143, WO 97/47386, WO 97/34692, WO 98/00413, WO 98/00414, WO 98/00415, WO 99/00188, WO 00/59632, WO 00/35893, WO 00/07964, as well as EP-A1-0,709,360 and U.S. Pat. No. 5,623,090. In a preferred form of the catalyst, the support is a titanium-containing or vanadium-containing support, more preferably, a titanium-containing support. In a preferred form of the catalyst, the catalytic metal is selected from the group consisting of gold, silver, the platinum group metals, the lanthanide rare earths, and combinations thereof The platinum group metals include ruthenium, rhodium, palladium, osmium, iridium, and platinum. The lanthanide rare earths include cerium, praseodymium, neodymium, samarium, europium, gadolinium, terbium, dysprosium, erbium, thulium, ytterbium, and lutetium. The catalytic metal can exist in any oxidation state that is available to the specific metal, so long as the catalyst produced therefrom exhibits activity in a hydro-oxidation process. Typical oxidation states include the zerovalent metallic state and any positive oxidation state ranging from greater than 0 to +3, as determined, for example, by X-ray-photoelectron spectroscopy (XPS) and neutron activation analysis (NAA). The catalytic metal can exist as ions or charged clusters, and/or as discrete metallic particles, and/or as mixed catalytic metal-promoter metal particles, and/or as atoms or clusters of atoms dispersed over the surface of the support. The metals in the support, such as vanadium and titanium, typically exist in a positive oxidation (non-metallic) state.

The loading of the catalytic metal on the support can vary widely, provided that the catalyst is active in a hydro-oxidation process. Generally, the total loading of catalytic metal(s) is greater than 10 parts per million by weight, and preferably greater than 0.010 weight percent, based on the total weight of the hydro-oxidation catalyst. More preferably, the total loading of catalytic metal(s) is greater than 0.01, and most preferably, greater than 0.03 weight percent. Generally, the total loading of catalytic metal(s) is less than 10, preferably, less than 5.0, and more preferably, less than 1.0 weight percent, based on the total weight of the hydro-oxidation catalyst.

Optionally, the hydro-oxidation catalyst may further comprise at least one promoter, which is defined as any metal or metallic ion that improves the productivity of the catalyst. Factors contributing to increased productivity include, for instance, increased conversion of the hydrocarbon reactant, increased selectivity to partially-oxidized product, decreased productivity to water, and increased catalyst lifetime. Preferably, the promoter is selected from the Group 1, Group 2, the lanthanide rare earths, and actinide metals, and combinations thereof. More preferably, the Group 1 metals include lithium, sodium, potassium, rubidium, and cesium. More preferably, the Group 2 metals include magnesium, calcium, strontium, and barium. More preferably, the lanthanides include cerium, praseodymium, neodymium, samarium, europium, gadolinium, terbium, dysprosium, erbium, thulium, ytterbium, and lutetium; and more preferably, the actinides include thorium and uranium. Most preferably, the promoter is selected from lithium, sodium, potassium, rubidium, cesium, magnesium, calcium, barium, erbium, lutetium, and combinations thereof Note that the lanthanide rare earths may fiinction as catalytic metals when essentially no other catalytic metal is present in the catalyst, as taught in WO 97/25143. Alternatively, the lanthanide rare earths maybe considered to function as promoters when other primary catalytic metals, such as gold and silver, are present in the catalyst, as taught, for example, in WO 98/00414.

The total quantity of promoter metal(s) loaded onto the catalyst is generally greater than 0.001, and preferably, greater than 0.01 weight percent, based on the total weight of the catalyst. The total quantity of promoter metal(s) loaded onto the catalyst is generally less than 20, and preferably, less than 15 weight percent, based on the total weight of the catalyst. Those skilled in the art will recognize that when a promoter metal titanate or promoter metal silicate is employed as the source of promoter, the weight percentage of promoter metal may be much higher, for example, as high as 80 weight percent.

The catalyst support may take any form, provided that the catalytic metal(s) and any optional promoter(s) can be affixed thereon, and provided that the catalyst synthesized therefrom exhibits hydro-oxidation activity. Non-limiting examples of suitable supports include amorphous and crystalline silicas, such as silicalite or MCM-41; aluminas; metallo-silicates, such as, aluminosilicates and titanosilicates; promoter metal silicates, such as, the silicates of Group 1, Group 2, the lanthanide, and actinide elements; and other common refractory oxides and similar support materials. Preferred supports include titanium-containing supports, vanadium-containing supports, and zirconia, as described in the following patent publications: WO 96/02323, WO 97/34692, WO 97/47386, WO 98/00413, WO 98/00414, WO 98/00415, WO 00/59632, U.S. Pat. Nso. 5,623,090, 5,939,569, WO 99/00188, and WO 00/35893. More preferred titanium-containing supports include porous crystalline titanosilicates of the prior art, such as TS-1, TS-2, Ti-beta, Ti-MCM-41, and Ti-MCM-48, as well as, stoichiometric and non-stoichiometric, crystalline and amorphous, promoter metal titanates. Preferably, the promoter metal titanate is selected from the group consisting of magnesium titanate, calcium titanate, barium titanates, strontium titanate, sodium titanate, potassium titanate, and the titanates of erbium, lutetium, thorium, and uranium. As a further alternative, amorphous and crystalline titanium oxides, including the anatase, rutile, and brookite phases of titanium dioxide, can be suitably employed as the titanium-containing support.

In those instances wherein titanium is affixed to a support, the titanium loading can be any loading that gives rise to an active hydro-oxidation catalyst. Typically, the titanium loading is greater than 0.02 weight percent, preferably, greater than 0.1 weight percent, based on the weight of the support. Typically, the titanium loading is less than 20 weight percent, and preferably, less than 10 weight percent, based on the weight of the support.

The silicon to titanium atomic ratio (Si:Ti) of the aforementioned titanosilicate supports can be any ratio that provides for an active hydro-oxidation catalyst. A generally advantageous Si:Ti atomic ratio is equal to or greater than 5:1, preferably, equal to or greater than 10:1. A generally advantageous Si:Ti atomic ratio is equal to or less than 500:1, preferably, equal to or less than 100:1.

In one preferred embodiment of the titanium-containing support, the support possesses a plurality (two or more) of titanium coordination environments, resulting in a plurality of titanium species, as taught in WO 00/59632. This modified titanosilicate comprises a quasi-crystalline material having an MFI structure code, as determined by X-ray diffraction (XRD), and possesses a plurality of titanium species, as determined by XPS and/or ultraviolet-visible diffuse reflectance spectroscopy (UV-VIS DRS). Another preferred titanium-containing support comprises a disorganized phase of titanium dispersed on a support material, preferably, silica. The disorganized phase of titanium does not exhibit an organized, periodic crystallinity and can be distinguished from bulk organized (crystalline) phase, such as crystalline titanium dioxide, by one or more analytical techniques, such as, high resolution transmission electron microscopy (HR-TEM), X-ray diffraction (XRD), and Raman spectroscopy. A preferred support containing disorganized phase titanium and its synthesis are described in international patent publication WO 98/00415. Another preferred support containing disorganized phase titanium and it alternative methods of preparation are described in WO 00/59632. Preferably, the disorganized titanium phase also contains a plurality of titanium coordination environments.

Any combination or mixture of titanium-containing supports described hereinabove can also be employed to advantage in the catalyst of this invention.

The catalyst support may be shaped into any form suitable for catalyst particles, for example, beads, pellets, spheres, honeycombs, monoliths, extrudates, and films. Optionally, the catalyst support can be extruded with, bound to, or supported on a second support for the purpose of binding together the catalyst particles and/or improving the catalyst's strength or attrition resistance. For example, it may be desirable to prepare a thin film of the catalyst support, for example, a titanium-containing support, on a secondary support that is shaped into a bead, pellet, or extrudate. The second support is typically inert in the process and need not contain catalyst metal(s). Suitable secondary supports include carbon and any refractory oxide, such as, silica, alumina, aluminosilicates; ceramics, including ceramic carbides and nitrides; and metallic supports. If a second support is used, the quantity of second support generally ranges from greater than 0 to 95 weight percent, based on the combined weight of the catalyst and second support.

There is no limitation on the method of incorporating the catalytic metal(s) and any optional promoter metal(s) onto the catalyst support, provided that the catalyst produced exhibits activity in a hydro-oxidation process. Non-limiting examples of suitable preparation methods include impregnation, deposition-precipitation, spray-drying, ion-exchange, vapor deposition, and solid-solid reaction. Impregnation and deposition-precipitation are somewhat preferred. In preparing one of the most preferred catalysts comprising gold on a titanium-containing support, the synthesis conditions are typically chosen to minimize the reduction of oxidized gold to metallic gold. Details of the deposition or impregnation of oxidized gold onto a titanium-containing support are set forth in WO 00/59632.

The catalytic metal and promoter metal depositions made by impregnation or deposition-precipitation typically are conducted at a temperature ranging from −10° C. to 100° C. Any compound containing the catalytic metal can be used to prepare the solution or suspension for the impregnation or deposition-precipitation, as the case may be. For the most preferred gold catalysts, suitable gold compounds include chloroauric acid, sodium chloroaurate, potassium chloroaurate, gold cyanide, potassium gold cyanide, gold acetate, diethylamine auric acid trichloride, alkyl gold halides, preferably, alkyl gold chlorides, and alkali aurates, such as lithium aurate, sodium aurate, potassium aurate, rubidium aurate, and cesium aurate. Organo-gold compounds can also be employed. For preparing the silver catalysts, suitable compounds include silver nitrate and silver carboxylates, such as silver oxalate and silver lactate. Any salt of the promoter metal can be used, for example, the promoter metal halides, such as the fluorides, chlorides, and bromides; promoter nitrates, borates, silicates, sulfates, phosphates, carbonates, and carboxylates, particularly the acetates, oxylates, cinnamates, lactates, maleates, and citrates; as well as any mixture of the aforementioned salts. Suitable solvents for the deposition(s) include, but are not limited to, water and organic solvents, the latter including alcohols (for example, methanol, ethanol, and isopropanol), esters, ketones, and aliphatic and aromatic hydrocarbons. Mixtures of water and organic solvents may also be employed. Typically, where the catalytic metal(s) and optional promoter(s) are deposited from solution onto the support, the molarity of the soluble catalytic metal compound or promoter compound ranges from 0.0001 M to the saturation point of the compound, preferably, from 0.0005 M to 0.5 M. If an aqueous solution is used, the pH of the solution may be adjusted to any value between 5 and 14, preferably, with a base selected, for example, from carbonates, borates, carboxylates, hydroxides, silicates, and mixtures thereof. The solution may also contain cationic and/or anionic additives which favor stabilization of oxidized species, preferably oxidized gold species. Suitable additives in this regard include certain promoter metal ions (for example, $Li^+$, $Mg^{+2}$, and $La^{+3}$), as well as halides, sulfates, phosphates, carbonates, borates, and carboxylates (for example, acetates, lactates, citrates, maleates, and cinnamates), and mixtures of any of the aforementioned additives. After the deposition, the support containing the catalytic metal(s) and optional promoter(s) is typically dried under air at a temperature between 20° C. and 120° C. to remove the solvent. Additional details of this type of deposition are given in WO 00/59632.

If necessary, the promoter metal(s) can be deposited onto the support simultaneously with the catalytic metal, or alternatively, in a separate step either before or after the catalytic metal is deposited. If necessary, the promoter metal(s) can be deposited onto the preferred titanium-containing support simultaneously with the titanium, or alternatively, in a separate step either before or after the titanium is added. For the purposes of this discussion, the word "deposit" will include all of the methods of deposition-precipitation, ion-exchange, and impregnation. Alternatively, the promoter metal can be deposited onto a precursor form of the catalyst before the titanium is added, or after it is added, or simultaneously with the titanium. After the promoter metal is deposited, washing is optional, and if done, the wash liquid preferably contains salts of the desired promoter metals.

In the unique process of this invention, the lifetime of a hydro-oxidation catalyst is improved by contacting the catalyst support with a hydroxy-functionalized organosilicon compound, a carboxy-functionalized organosilicon compound, or a mixture of hydroxy-functionalized and carboxy-functionalized organosilicon compounds. It should be recognized that a single organosilicon compound may also contain both hydroxy and carboxy functionalities. The hydroxy-functionalized organosilicon compound can be any which contains silicon, one or more organic moieties bound to silicon, and one or more hydroxy moieties bound to silicon or the organic moiety. Suitable hydroxy-functionalized organosilicon compounds include organosilanols, organosiliconates, hydroxy-functionalized organosilanes, hydroxy-functionalized organosiloxanes, hydroxy-functionalized organosilazanes, hydroxy-functionalized organosilylamines, and hydroxy-functionalized organosilylamides. In one preferred embodiment, the hydroxy-functionalized organosilicon compound is represented by the following formula:

$$(R)_x-Si-(O^-M^+)_y \qquad (I)$$

wherein each R is independently selected from the group consisting of $C_{1-15}$ alkyl, $C_{1-15}$ aryl, $C_{1-15}$ hydroxyalkyl, and $C_{1-15}$ hydroxyaryl moieties; each $M^+$ is independently an inorganic or organic ion of +1 charge, preferably, $H^+$ or a Group 1 cation; x is an integer ranging from 1 to 4; y is an integer ranging from 0 to 3; the total (x+y) equals 4; with the proviso that when y=0 and x=4, then at least one R moiety is hydroxy-functionalized; and with the added proviso that when no R is hydroxy-functionalized, then at least one $M^+$ is $H^+$. Non-limiting examples of suitable hydroxy-functionalized organosilicon compounds that satisfy the aforementioned formula include sodium methylsiliconate, trimethylsilanol, triethylsilanol, triphenylsilanol, 2-(trimethylsilyl) ethanol, t-butyldimethylsilanol, diphenylsilanol, and trimethylsilyl-propargyl alcohol. Another preferred hydroxy-substituted organosilicon compound may be represented by the following formula:

   (II)

wherein each R' is independently selected from the group consisting of $C_{1-15}$ alyl, $C_{1-15}$ aryl, $C_{1-15}$ hydroxyalkyl, and $C_{1-15}$ hydroxyaryl moieties; each $M'^+$ is independently an inorganic or organic ion of +1 charge, preferably, $H^+$ or a Group 1 ion; each v and v' is independently an integer from 1 to 3; each w and w' is independently an integer from 0 to 2; the total (v+w)=3; the total (v'+w')=3; with the proviso that when w or w' is 0 and v or v', respectively, is 3, then at least one R' moiety associated with the v or v', respectively, is hydroxy-functionalized; and with the added proviso that when v or v' is 0, then at least one of the M or M', respectively, is $H^+$. Suitable hydroxy-functionalized organosiloxanes, which may be represented by the aforementioned formula, include 1,3-bis(hydroxybutyl)tetramethyldisiloxane, and 1,3-bis(hydroxyethyl)tetramethyldisiloxane. Other suitable hydroxy-functionalized organosilicon compounds include silylated sugars, such as N-(3-triethoxysilylpropyl)-gluconamide. Most preferably, the organic siliconate is sodium methyl siliconate.

The carboxy-functionalized organosilicon compound can be any which contains silicon, one or more organic moieties, and one or more carboxy moieties. Either the acid or salt form of the carboxy moiety is acceptable. Typically, in these organosilicon compounds, the carboxy functionality is located on the organo component; however, carboxy functionalities bound to silicon may also be suitably employed. Carboxy-functionalized organosilicon compounds include, without limitation, carboxy-functionalized organosilanes, carboxy-functionalized organosilanols, carboxy-functionalized organosiliconates, carboxy-functionalized organosiloxanes, carboxy-functionalized organosilazanes, carboxy-functionalized organosilylamines, and carboxy-functionalized organosilylamides. Non-limiting examples of suitable carboxy-functionalized organosilicon compounds include 1,3-bis-3-carboxypropyltetramethyl disiloxane, 2-(trimethylsilyl)acetic acid, 3-trimethylsilylpropionic acid, and salts (for example, alkali salts) of the aforementioned compounds. A preferred carboxy-functionalized organosilicon compound may be represented by the following formula:

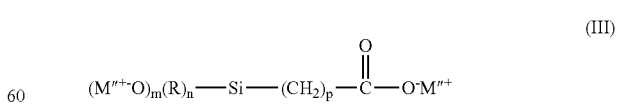   (III)

wherein each M" is independently an inorganic ion or organic radical of +1 charge, preferably, $H^+$, a Group 1 cation, or an R radical as noted hereinafter; each R is independently selected from the group consisting of $C_{1-15}$ alkyl, $C_{1-15}$ aryl, $C_{1-15}$ hydroxyalkyl, and $C_{1-15}$ hydroxyaryl moieties; m and n are each integers from 0 to 3, such that the sum of m+n=3; and p is an integer from 1 to 15. An even more preferred carboxy-functionalized organosilicon compound is 1,3-bis-3-carboxypropyl-tetramethyl disiloxane.

Particularly advantageous hydroxy-functionalized or carboxy-functionalized organosilicon compounds contain three chemically distinct components: the silicon moiety, at least one hydroxy or carboxy moiety, and in addition, at least one promoter cation, the suitable promoters being described hereinabove. While not being bound to theory, it is believed that the silicon moiety aids in increasing catalyst lifetime, while the promoter cation aids in maintaining high catalyst activity and selectivity. It is also believed that the hydroxy or carboxy functionality aids in the deposition of the catalytic metal ions, for example, gold, silver, platinum group metal ions, onto the support. Sodium methyl siliconate and the sodium salt of 2-(trimethyl-silyl)acetic acid are illustrative of preferred hydroxy and carboxy-functionalized organosilicon compounds that provide this triple functionality.

The amount of hydroxy-functionalized or carboxy-functionalized organosilicon compound that is used in the process of this invention can be varied over a wide range, so long as the catalyst prepared therefrom exhibits an enhanced lifetime, as compared with a similar catalyst wherein the organosilicon compound is not employed. Normally, greater than 0.005 mole, and preferably, greater than 0.1 mole hydroxy- or carboxy-functionalized organosilicon compound is used per mole of catalytic metal present in the catalyst. Normally, less than 20 moles, and preferably, less than 10 moles hydroxy- or carboxy-functionalized organosilicon compound are used per mole of catalytic metal present in the catalyst.

The lifetime enhancement treatment is effected by contacting the catalyst support with the hydroxy-functionalized or carboxy-functionalized organosilicon compound, before, during, or after adding the catalytic metal(s) and promoter (s). In a most preferred embodiment, the support is contacted with the hydroxy- or carboxy-functionalized organosilicon compound simultaneously with the deposition of the catalytic metal(s) and any optional promoter(s). The hydroxy-functionalized or carboxy-functionalized organosilicon compound may be provided as a gas, a neat liquid, or dissolved in an appropriate solvent. Suitable solvents include, for example, water, alcohols, such as methanol, ethanol, and 2-propanol; ketones, such as acetone and methyl ethyl ketone; ethers, such as di(isopropyl) ether and tetrahydrofuran; esters, such as ethyl acetate; and hydrocarbon solvents, such as toluene and xylene. Normally, the organosilicon compound is provided in solution, typically in a concentration ranging from 0.01 M to the saturation point of the organosilicon compound, which is typically less than 5 M. The contacting of the support with the organosilicon compound may be conducted at a temperature ranging from −10° C. to the boiling point of any solvent that is present. Preferably, the contacting temperature is greater than −5° C. Preferably, the contacting temperature is less than 100° C. The contacting time varies depending upon the particular support and hydroxy or carboxy-functionalized organosilicon compound employed, as well as the particular contacting temperature. Generally, a treatment time ranging from 30 seconds to 2 hours is sufficient.

After deposition of the catalytic metal(s) and any promoter metal(s) and additives, and after contacting the support with the organosilicon compound, the as-synthesized catalyst may be used without further treatment. Alternatively, the as-synthesized catalyst may be calcined under air, or heated in an inert atmosphere, such as nitrogen. The calcination/heating temperature depends upon the particular sample, but may be varied from 100° C. to 800° C., preferably, from 120° C. to 750° C. If gold is used as the catalytic metal, then preferably, the temperature is chosen to minimize the reduction of oxidized gold to metallic gold. As an alternative, the as-synthesized catalyst may be conditioned prior to use. The conditioning comprises heating the catalyst, for example, in the oxidation reactor under an atmosphere comprising an inert gas, such as helium, and optionally, one or more compounds selected from hydrocarbons (for example, an alkane or olefin to be oxidized), hydrogen, and oxygen at a temperature between ambient, taken as 21° C., and 600° C.

The aforementioned catalyst is useful in hydro-oxidation processes, preferably, those described in international patent publications WO 98/00413, WO 98/00414, WO 98/00415, WO 99/00188, and WO 00/59632. In the hydro-oxidation process, a reactant hydrocarbon, such as an alkane or an olefin, is contacted with oxygen in the presence of hydrogen and the hydro-oxidation catalyst, and optionally a diluent, to yield a partially-oxidized hydrocarbon, such as an alcohol, aldehyde, ketone, olefin oxide, and/or carboxylic acid. In one preferred embodiment, an alkane is employed to produce an alcohol or ketone. In another preferred embodiment, an olefin is employed to produce an olefin oxide. Preferably, the hydrocarbon is a $C_{1-20}$ hydrocarbon. More preferably, the hydrocarbon is an olefin having three or more carbon atoms, including monoolefins, diolefins, and olefins substituted with various organic moieties. Even more preferred are $C_{3-8}$ olefins; the most preferred olefin is propylene. Typically, the quantity of reactant hydrocarbon in the feedstream is greater than 1, preferably, greater than 10, and more preferably, greater than 20 mole percent, based on the total moles of reactant hydrocarbon, oxygen, hydrogen, and optional diluent. Typically, the quantity of reactant hydrocarbon is less than 99, preferably, less than 85, and more preferably, less than 70 mole percent, based on the total moles of reactant hydrocarbon, oxygen, hydrogen, and optional diluent. Preferably, the quantity of oxygen in the feedstream is greater than 0.01, more preferably, greater than 1, and most preferably greater than 5 mole percent, based on the total moles of reactant hydrocarbon, hydrogen, oxygen, and optional diluent. Preferably, the quantity of oxygen is less than 30, more preferably, less than 25, and most preferably less than 20 mole percent, based on the total moles of reactant hydrocarbon, oxygen, hydrogen, and optional diluent. Suitable quantities of hydrogen in the feedstream are typically greater than 0.01, preferably, greater than 0.1, and more preferably, greater than 3 mole percent, based on the total moles of reactant hydrocarbon, hydrogen, oxygen, and optional diluent. Suitable quantities of hydrogen are typically less than 50, preferably, less than 30, and more preferably, less than 20 mole percent, based on the total moles of reactant hydrocarbon, hydrogen, oxygen, and optional diluent.

The diluent can be any gas or liquid that does not inhibit the process of this invention. In a gas phase process, suitable gaseous diluents include, but are not limited to, helium, nitrogen, argon, methane, carbon dioxide, steam, and mixtures thereof. In a liquid phase process, the diluent can be any oxidation stable and thermally stable liquid. Suitable liquid diluents include chlorinated aromatics, preferably chlorinated benzenes, such as chlorobenzene and dichlorobenzene; chlorinated aliphatic alcohols, preferably $C_{1-10}$ chlorinated alkanols, such as chloropropanol; as well as liquid polyethers, polyesters, and polyalcohols. If used, the amount of diluent in the feedstream is typically greater than 0, preferably greater than 0.1, and more preferably, greater than 15 mole percent, based on the total moles of reactant hydrocarbon, oxygen, hydrogen, and optional diluent. The amount of diluent is typically less than 90, preferably, less than 80, and more preferably, less than 70 mole percent, based on the total moles of reactant hydrocarbon, oxygen, hydrogen, and diluent.

The hydro-oxidation process can be conducted in a reactor of any conventional design suitable for gas or liquid phase processes. Generally, the process is conducted at a temperature that is greater than ambient, taken as 20° C., and less than 250° C. Since catalysts prepared by the method of this invention advantageously produce low amounts of water, the hydro-oxidation process can be conducted at temperatures higher than those used in many prior art hydro-oxidation processes. Preferably, the temperature is greater than 70° C., more preferably, greater than 120° C. Preferably, the temperature is less than 225° C. Operation at higher temperatures provides steam credits from the heat produced. Accordingly, the hydro-oxidation process can be integrated into a total plant design wherein the heat derived from the steam is used to drive additional processes, such as the separation of the partially-oxidized products from water.

In preferred operation, the pressure of the hydro-oxidation process ranges from atmospheric to 400 psig (2758 kPa), more preferably, from 150 psig (1034 kPa) to 250 psig (1724 kPa). For a gas phase process the gas hourly space velocity (GHSV) of the reactant hydrocarbon can vary over a wide range, but typically is greater than 10 ml reactant hydrocarbon per ml catalyst per hour ($h^{-1}$), preferably greater than 100 $h^{-1}$, and more preferably, greater than 1,000 $h^{-1}$. Typically, the GHSV of the reactant hydrocarbon is less than 50,000 $h^{-1}$, preferably, less than 35,000 $h^{-1}$, and more preferably, less than 20,000 $h^{-1}$. The gas hourly space velocities of the oxygen, hydrogen, and diluent components can be determined from the space velocity of the reactant hydrocarbon taking into account the relative molar ratios desired.

In the process of this invention, the activity of the catalyst can be measured by the "conversion of reactant hydrocarbon," that term being defined as the mole or weight percentage of reactant hydrocarbon in the feedstream that reacts to form products. Generally, the conversion of reactant hydrocarbon, which is achieved, is greater than 0.25 mole percent, preferably, greater than 1.0 mole percent, and more preferably, greater than 2.0 mole percent. Advantageously, the selectivity to partially-oxidized products, such as olefin oxide, is high at the aforementioned conversions. The "selectivity" is defined as the mole or weight percentage of reacted hydrocarbon that forms a specified partially-oxidized product, such as alcohol, ketone, or olefin oxide. Generally, when the reactant hydrocarbon is an olefin, a selectivity to olefin oxide is achieved that is greater than 60 mole percent, preferably, greater than 70 mole percent, more preferably, greater than 80 mole percent, and in many instances, most preferably greater than 90 mole percent.

As a further advantage, an acceptable hydrogen efficiency is achieved in the hydro-oxidation process of this invention. Hydrogen efficiency is measured as the ratio of moles of water produced to moles of oxygenated product produced. Hydrogen efficiency can be optimized by achieving a molar ratio of water to oxygenated product, for instance, olefin oxide, as low as possible. In the process of this invention, the molar ratio of water to oxygenated product is typically greater than 2:1, but less than 10:1, and more preferably, less than 5:1.

The productivity of the catalyst of this invention is also beneficially high, the term "productivity" being defined, for the purposes of this invention, as the kilograms of partially-oxidized hydrocarbon product formed per kilogram of catalyst per hour. In the process of this invention, the productivity is typically greater than 30 g oxidized product/kg cat-hr, preferably, greater than 50 g oxidized product/kg cat-hr, and more preferably, greater than 100 g oxidized product/kg cat-hr.

When activity of the hydro-oxidation catalyst has decreased to an unacceptably low level, the catalyst may be regenerated by various means. One method may comprise heating the deactivated catalyst at a temperature between 150° C. and 500° C. in a regeneration gas containing hydrogen, oxygen, water, or mixtures thereof, and optionally containing an inert gas, at a temperature preferably between 200° C. and 400° C. Suitable inert gases are non-reactive and include, for example, nitrogen, helium, and argon. Preferably, the total amount of hydrogen, oxygen, water, or mixture thereof comprises from 2 to 100 mole percent of the regeneration gas including optional inert gas.

The invention will be further clarified by a consideration of the following examples, which are intended to be purely exemplary of the use of the invention. Other embodiments of the invention will be apparent to those skilled in the art from a consideration of this specification or practice of the invention as disclosed herein.

EXAMPLE 1

A titanosilicate support comprising a plurality of titanium species was prepared as described in Example 7 of WO 00/59632.

A catalyst comprising oxidized gold, a hydroxy-functionalized organosilicon compound, and the aforementioned titanium-containing support was prepared as follows. With magnetic stirring cesium hydroxide (0.34 g, 50 weight percent aqueous solution) was added to deionized water (20.04 g). The solution was stirred for 5 min; then fumaric acid (0.108 g) was added to the solution. The solution was stirred for 10 min until the acid was fully dissolved. Thereafter, sodium methyl siliconate (0.35 g, 30 weight percent aqueous solution) was added to the solution containing the fumaric acid and cesium salt, and the resulting solution was stirred for 5 min. Tetrachloroauric acid (0.0008 g) was added to the solution with stirring. The solution turned light yellow on adding the gold salt, but became clear after 10 min of stirring. The titanosilicate (5.0 g as chunks) was heated for 1 h under vacuum in a flask attached to a rotary evaporator positioned in a water bath at 80° C. The titanosilicate was then cooled to room temperature and impregnated with the gold-containing solution (7.5 g) under dynamic vacuum. While on the rotary evaporator, the flask was rotated at room temperature under vacuum for 2 h. Thereafter, the impregnated titanosilicate was heated under vacuum for 4 h at 80° C., and then the flask was cooled to room temperature to obtain the catalyst of this invention. The catalyst had a white color, which indicated the presence of oxidized gold.

The catalyst was evaluated in the hydro-oxidation of propylene to form propylene oxide as follows. The catalyst (3 g) was loaded into a fixed-bed, continuous flow reactor [0.5 inch (12.5 mm) diameter×12 inches (30 cm) length)] and activated as follows. At 140° C., the catalyst was heated under helium for 5 hours, then heated under a flow of propylene and hydrogen for 10 min, then oxygen was added. Feedstream composition was 35 percent propylene, 10 percent oxygen, 10 percent hydrogen, and 45 percent helium.

Propylene, oxygen and helium were used as pure streams; hydrogen was mixed with helium in a 20 $H_2$/80 He (v/v) mixture. Total flow was 1,500 standard cm³ per minute (sccm). After a constant rate of propylene oxide production was obtained for 1 hour, the temperature was ramped in 15° C. intervals up to the operating temperature. Operating pressure was 225 psig. Products were analyzed using on-line gas chromatography (Chrompack® Poraplo™ S column, 25 m). The propylene oxide productivity is set forth in Table 1.

TABLE 1

Hydro-oxidation of Propylene to Propylene Oxide

| | Temperature | | | | | |
|---|---|---|---|---|---|---|
| | 150° C. | | 160° C. | | 170° C. | |
| | Time on Stream (hr) | | | | | |
| | 3 hr | 15 hr | 20 hr | 39 hr | 46 hr | 65 hr |
| Example 1[a] Productivity (g PO per kg cat-hr)[b] | 150 | 160 | 226 | 250 | 338 | 336 |
| Comparative Exp. 1[a] Productivity (g PO per kg cat-hr)[b] | 146 | 128 | 169 | 155 | 197 | 174 |

[a]Feedstream composition: 35 percent propylene, 10 percent oxygen, 10 percent hydrogen, and 45 percent helium; total flow, 1,500 sccm; 225 psig.
[b]Productivity given as grams propylene oxide (PO) per kg catalyst per hour (g PO per kg cat-hr).

From Table 1, it is seen that the propylene oxide (PO) productivity steadily increased from 150 g PO/kg cat-hr at 150° C. and 3 hours on stream to 336 g PO/kg cat-hr at 170° C. and 65 hours on stream. It was also observed that at 150° C., the PO selectivity was 97.5 mole percent, and the $H_2O$/PO molar ratio was 3.2/1.

COMPARATIVE EXPERIMENT 1

Example 1 was repeated, with the exception that the treatment with sodium methyl siliconate was eliminated from the catalyst preparation. The comparative catalyst was evaluated in the hydro-oxidation of propylene in the manner described in Example 1, with the results shown in Table 1. It was seen that the propylene oxide (PO) productivity varied throughout the run from 146 g PO/kg cat-hr at 150° C. and 3 hours on stream, to 197 g PO/kg cat-hr at 170° C. and 46 hours on stream, to 174 g PO/kg cat-hr at 170° C. and 65 hours on stream. At 150° C., a selectivity to propylene oxide of 97.0 mole percent, and a $H_2O$/PO molar ratio of 2.7/1 were achieved. When Example 1 was compared with Comparative Experiment 1, it was seen that the catalyst of the invention, treated with the hydroxy-substituted organosilicon compound, achieved a significantly higher propylene oxide productivity for a longer time than the comparative catalyst that was not treated. Selectivities to propylene oxide and hydrogen efficiency, as measured by the molar ratio of water to propylene oxide, were comparable in both experiments.

EXAMPLE 2

A catalyst comprising oxidized gold, a carboxy-functionalized organosilicon compound, and the titanium-containing support of Example 1 was prepared as follows. With magnetic stirring cesium hydroxide (0.29 g, 50 weight percent aqueous solution) was added to deionized water (19.85 g). The solution was stirred for 5 min; then 1,3-bis-(2-carboxypropyl)-tetramethyldisiloxane (0.143 g) was added. The solution was stirred for 10 min. Tetrachloroauric acid (0.007 g) was added to the solution with stirring. The titanosilicate (5.0 g as chunks) was heated for 1 h under vacuum in a flask attached to a rotary evaporator positioned in a water bath at 80° C. The titanosilicate was then cooled to room temperature and impregnated with the gold-containing solution (7.5 g) under dynamic vacuum. While on the rotary evaporator, the flask was rotated at room temperature under vacuum for 2 h. Thereafter, the impregnated titanosilicate was heated under vacuum for 1 h at 80° C., and then the flask was cooled to room temperature to obtain the catalyst of this invention. The catalyst had a white color, which indicated the presence of oxidized gold.

The catalyst was evaluated in the hydro-oxidation of propylene to form propylene oxide as follows. The catalyst (2 g) was loaded into a fixed-bed, continuous flow reactor [0.5 inch (12.5 mm) diameter×12 inches (30 cm) length)] and activated as follows. At 140° C., the catalyst was heated under helium for 2 hours, then heated under a flow of propylene and hydrogen for 10 min, then oxygen was added. Feedstream composition was 20 percent propylene, 10 percent oxygen, 10 percent hydrogen, and 60 percent helium. Propylene, oxygen and helium were used as pure streams; hydrogen was mixed with helium in a 20 $H_2$/80 He (v/v) mixture. Total flow was 160 standard cm³ per minute (sccm). After a constant rate of propylene oxide production was obtained for 1 hour, the temperature was ramped in 10° C. intervals up to the operating temperature. Operating pressure was 15 psig. Products were analyzed using on-line gas chromatography (Chrompack™ Poraplo™ S column, 25 m). The propylene oxide productivity is set forth in Table 2.

TABLE 2

Hydro-oxidation of Propylene to Propylene Oxide

| | Temperature (° C.) | | | | | |
|---|---|---|---|---|---|---|
| | 150° C. | | 160° C. | | 180° C. | |
| | Time on Stream (hr) | | | | | |
| | 27 hr | 37 hr | 38 hr | 47 hr | 48 hr | 52 hr |
| Example 2[a] Productivity (g PO per kg cat-hr)[b] | 10.7 | 10.6 | 13.5 | 13.8 | 22.0 | 22.3 |
| Comparative Exp. 2[a] Productivity (g PO per kg cat-hr)[b] | 8.5 | 7.7 | 10.6 | 9.6 | 16.1 | 14.7 |

[a]Feedstream composition: 20 percent propylene, 10 percent oxygen, 10 percent hydrogen, and 60 percent helium; total flow, 160 sccm; 15 psig.
[b]Productivity given as grams propylene oxide (PO) per kg catalyst per hour (g PO per kg cat-hr).

From Table 2, it was seen that the productivity of propylene oxide increased steadily from a value of 10.7 g PO/kg cat-hr at 150° C. and 27 hours on stream to a value of 22.0 g PO/kg cat-hr at 180° C. and 48 hours on stream. Moreover, at 150° C., a selectivity to propylene oxide of 99 mole percent and a $H_2O$/PO molar ratio of 3.6/1 were achieved.

COMPARATIVE EXPERIMENT 2

Example 2 was repeated, with the exception that the treatment with 1,3-bis (2-carboxypropyl)tetramethyldisiloxane was eliminated from the catalyst preparation. The comparative catalyst was evaluated in the hydro-oxidation of propylene in the manner described in Example 2, with the results shown in Table 2. It is seen that in the absence of organosilicon compound, the catalyst activity varied over the run. A productivity of 8.5 g PO/kg cat-hr was achieved at 150° C. and 27 hours on stream. A productivity of 16.1 g PO/kg cat-hr was achieved at 180° C. and 48 hours on stream. Moreover, at 1500° C., a selectivity to propylene oxide of 99 mole percent, and a $H_2O$/PO molar ratio of 3.6/1 were achieved. When Example 2 was compared with Comparative Experiment 2, it was seen that the catalyst of the invention, treated with the carboxy-substituted organosilicon compound, achieved a higher propylene oxide productivity for a longer time than the comparative catalyst that was not treated. Selectivities to propylene oxide and hydrogen efficiency, as measured by the molar ratio of water to propylene oxide, were comparable in both experiments.

What is claimed is:

1. A method of increasing the lifetime of a hydro-oxidation catalyst comprising at least one catalytic metal on a catalyst support, the hydro-oxidation catalyst being prepared by depositing one or more catalytic metals onto the catalyst support, the method of increasing lifetime comprising contacting the catalyst support with a hydroxy-functionalized organosilicon compound, a carboxy-functionalized organosilicon compound, or a mixture thereof prior to, simultaneous with, or after depositing the one or more catalytic metals onto the catalyst support and under conditions sufficient to increase the catalyst lifetime.

2. The method of claim 1 wherein the catalytic metal is selected from the group consisting of gold, silver, the platinum group metals, the rare earth lanthanides, and mixtures thereof.

3. The method of claim 1 wherein the catalytic metal is gold, silver, or a mixture thereof.

4. The method of claim 1 wherein the catalyst further comprises one or more promoters, which are deposited onto the catalyst support prior to, simultaneously with, or after deposition of the one or more catalytic metals onto the catalyst support.

5. The method of claim 4 wherein the promoter is selected from Group 1, Group 2, the lanthanide rare earths, the actinides, and mixtures thereof.

6. The method of claim 4 wherein the promoter is selected from the group consisting of lithium, sodium, potassium, rubidium, cesium, magnesium, calcium, barium, erbium, lutetium, and mixtures thereof.

7. The method of claim 1 wherein the support is a titanium-containing or a vanadium-containing support.

8. The method of claim 7 wherein the support is a titanium-containing support, which is selected from the group consisting of titania, titanosilicates, titanium dispersed on silica, promoter metal titanates, titanium dispersed on promoter metal silicates, and mixtures thereof.

9. The method of claim 1 wherein the catalyst further comprises an additive selected from the group consisting of promoter metal halides, sulfates, phosphates, carbonates, borates, carboxylates, and mixtures thereof, which additive is deposited onto the catalyst support simultaneously with the deposition of the one or more catalytic metals or optional one or more promoters onto the support.

10. The method of claim 1 wherein the organosilicon compound is represented by the following formula:

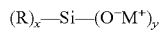

wherein each R is independently selected from the group consisting of $C_{1-15}$ alkyl, $C_{1-15}$ aryl, $C_{1-15}$ hydroxyalkyl, and $C_{1-15}$ hydroxyaryl moieties; each M is independently selected from $H^+$ and inorganic and organic cations of +1 charge; x is an integer ranging from 1 to 4; y is an integer ranging from 0 to 3; and (x+y)=4; with the proviso that when y=0 and x=4, then at least one R moiety is hydroxy-functionalized; and with the further proviso that when no R is hydroxy-functionalized, then at least one $M^+$ is $H^+$.

11. The method of claim 1 wherein the hydroxy-functionalized organosilicon compound is represented by the following formula:

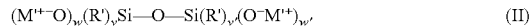

wherein each R' is independently selected from the group consisting of $C_{1-5}$ alkyl, $C_{1-15}$ aryl, $C_{1-15}$ hydroxyalkyl, and $C_{1-15}$ hydroxyaryl moieties; each $M'^+$ is $H^+$ or an inorganic or organic ion of +1 charge; each v and v' is independently an integer from 1 to 3; each w and w' is independently an integer from 0 to 2; the total (v+w)=3; the total (v'+w')=3; with the proviso that when w or w' is 0 and v or v', respectively, is 3, then at least one R' moiety associated with the v or v', respectively, is hydroxy-functionalized; and with the further proviso that when v or v' is 0, then at least one M or M', respectively, is H.

12. The method of claim 1 wherein the hydroxy-functionalized organosilicon compound is selected from the group consisting of sodium methylsiliconate, trimethylsilanol, triethylsilanol, triphenylsilanol, 2-(trimethylsilyl)ethanol, t-butyldimethylsilanol, diphenylsilanol, 1,3-bis(hydroxybutyl)tetramethyldisiloxane, N-(3-triethoxysilylpropyl)gluconamide, and trimethylsilylpropargyl alcohol.

13. The method of claim 1 wherein the carboxy-functionalized organosilicon compound is selected from the group consisting of 1,3-bis-3-carboxypropyltetramethyl disiloxane, 2-trimethylsilylacetic acid, 3-trimethylsilylpropionic acid, and salts of the aforementioned compounds.

14. The process of claim 1 wherein the carboxy-functionalized organosilicon compound is represented by the following formula:

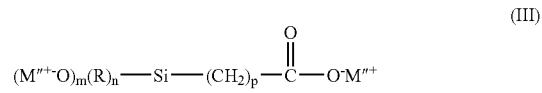

wherein each M″ is independently an inorganic ion or organic radical of +1 charge; R is independently selected from the group consisting of $C_{1-15}$ alkyl, $C_{1-15}$ aryl, $C_{1-15}$ hydroxyalkyl, and $C_{1-15}$ hydroxyaryl moieties; m and n are each independently an integer ranging from 0 to 3, such that the sum of m+n=3; and p is an integer ranging from 1 to about 15.

15. The method of claim 1 wherein the amount of hydroxy-functionalized or carboxy-functionalized organosilicon compound that is used ranges from greater than 0.005 mole to less than 20 moles, per mole of catalytic metal on the support.

16. The method of claim 1 wherein the support is contacted with a solution containing the organosilicon compound in a concentration ranging from 0.01 M to less than 5 M.

17. The method of claim 1 wherein the contacting of the support with the organosilicon compound is conducted at a temperature greater than −10° C. and less than 100° C.

18. The method of claim 1 wherein the support is contacted with the organosilicon compound for a time ranging from 30 seconds to 2 hours.

19. A composition comprising a catalytic metal selected from gold, silver, the platinum group metals, the lanthanide metals, and mixtures thereof, and optionally one or more promoter(s) on a titanium-containing support, the support being contacted with a hydroxy-functionalized organosilicon compound, a carboxy-functionalized organosilicon compound, or a mixture thereof.

20. The composition of claim 19 wherein the catalytic metal is gold, silver, or a mixture of gold and silver.

21. The composition of claim 19 wherein the support is selected from the group consisting of titania, titanosilicates, titanium dispersed on silica, promoter metal titanates, titanium dispersed on promoter metal silicates, and mixtures thereof.

22. The composition of claim 19 wherein the catalytic metal is oxidized gold; the titanium-containing support is a titanosilicate or titanium dispersed on silica; and wherein the support contains a plurality of titanium coordination environments; and optionally, the catalyst further comprises one or more promoter elements.

23. The composition of claim 19 wherein the promoter element is selected from the group consisting of Group 1, Group 2, the lanthanide rare earths, the actinides, and combinations thereof.

24. The composition of claim 19 wherein the promoter element is selected from the group consisting of lithium, sodium, potassium, rubidium, cesium, magnesium, calcium, barium, erbium, lutetium, and mixtures thereof.

25. A process of preparing a partially-oxidized hydrocarbon comprising contacting a hydrocarbon with oxygen in the presence of hydrogen and a hydro-oxidation catalyst comprising at least one catalytic metal on a catalyst support, the contacting being conducted under reaction conditions sufficient to prepare a partially-oxidized hydrocarbon, the catalyst being further characterized in that prior to use the catalyst support has been contacted with a hydroxy-functionalized organosilicon compound, a carboxy-functionalized organosilicon compound, or a mixture thereof.

26. The process of claim 25 wherein the hydrocarbon is an olefin, and the partially-oxidized hydrocarbon is an olefin oxide.

27. The process of claim 26 wherein the olefin is propylene, and the olefin oxide is propylene oxide.

28. The process claim 25 wherein the catalyst comprises gold, silver, or a combination thereof, and optionally, at least one promoter element selected from Group 1, Group 2, the lanthanide rare earths, the actinides, and combinations thereof on a titanium-containing support.

29. The process of claim 28 wherein the gold is predominantly oxidized gold, and the titanium-containing support contains a plurality of titanium coordination environments.

30. A method of increasing the lifetime of a hydro-oxidation catalyst comprising at least one catalytic metal on a catalyst support, the hydro-oxidation catalyst being prepared by depositing one or more catalytic metals onto the catalyst support, the method of increasing lifetime comprising contacting the catalyst support with a hydroxy-functionalized and/or carboxy-functionalized organosilicon compound simultaneously with the deposition of the catalytic metal(s).

* * * * *